US009936969B2

(12) United States Patent
Vincenot et al.

(10) Patent No.: US 9,936,969 B2
(45) Date of Patent: Apr. 10, 2018

(54) METHOD AND APPARATUS FOR GENERATING FOCUSED ULTRASONIC WAVES WITH SURFACE MODULATION

(75) Inventors: Jeremy Vincenot, Les Haies (FR); David Melodelima, Ruy (FR); Emmanuel Blanc, Saint-Didier au Mont d'Or (FR); Jean-Yves Chapelon, Villeurbanne (FR)

(73) Assignees: EDAP TMS FRANCE, Vaulx-en-Velin (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 554 days.

(21) Appl. No.: 14/007,918

(22) PCT Filed: Mar. 15, 2012

(86) PCT No.: PCT/FR2012/050544
§ 371 (c)(1),
(2), (4) Date: Dec. 3, 2013

(87) PCT Pub. No.: WO2012/131212
PCT Pub. Date: Oct. 4, 2012

(65) Prior Publication Data
US 2014/0180320 A1 Jun. 26, 2014

(30) Foreign Application Priority Data
Mar. 30, 2011 (FR) ..................................... 11 52657

(51) Int. Cl.
*A61B 17/32* (2006.01)
*G10K 11/32* (2006.01)

(52) U.S. Cl.
CPC ...... *A61B 17/320068* (2013.01); *G10K 11/32* (2013.01)

(58) Field of Classification Search
CPC ......... A61B 8/4477–8/4494; A61N 2007/0065
See application file for complete search history.

(56) References Cited

U.S. PATENT DOCUMENTS 4,281,550 A * 8/1981 Erikson ................ G01N 29/262 310/334
4,470,308 A * 9/1984 Hayakawa ............ B06B 1/0633 367/150
(Continued)

FOREIGN PATENT DOCUMENTS

EP 0401027 A2 12/1990
EP 0689187 B1 1/2002
(Continued)

OTHER PUBLICATIONS

International Search Report dated Jul. 23, 2012, corresponding to PCT/FR2012/050544.
(Continued)

*Primary Examiner* — Serkan Akar
(74) *Attorney, Agent, or Firm* — Ladas & Parry LLP

(57) ABSTRACT

The invention relates to a method for generating ultrasonic waves focused on a focal zone (5) in order to carry out biological lesions, comprising the activation of a plurality of ultrasonic transducer elements (3).
According to the invention:
- a target zone, in which homogenization of the supply of energy of the ultrasonic waves emitted by the ultrasonic transducer elements is desired, is chosen,
- the focusing effect and the acoustic attenuations of the ultrasonic waves on their path between the target zone and the ultrasonic transducer elements (3) are determined,
- the focusing effect and the acoustic attenuations of the ultrasonic waves are compensated, with ultrasonic transducer elements (3) at least some of which have (Continued)

non-identical emission surfaces such that in the target zone, the supply of energy of the ultrasonic waves emitted by the different ultrasonic transducer elements (3) is more or less identical.

13 Claims, 4 Drawing Sheets

(56) References Cited

U.S. PATENT DOCUMENTS

| | | | | |
|---|---|---|---|---|
| 4,888,746 | A | 12/1989 | Wurster et al. | |
| 5,165,414 | A | 11/1992 | Larson | |
| 5,922,962 | A | 7/1999 | Ishrak et al. | |
| 6,328,695 | B1 * | 12/2001 | Vammen | A61B 8/0875 600/442 |
| 6,543,272 | B1 * | 4/2003 | Vitek | A61N 7/02 601/2 |
| 7,678,054 | B2 | 3/2010 | Okazaki et al. | |
| 2007/0106157 | A1 * | 5/2007 | Kaczkowski | A61B 5/015 600/438 |
| 2009/0281463 | A1 * | 11/2009 | Chapelon | A61N 7/02 601/2 |
| 2012/0191020 | A1 * | 7/2012 | Vitek | A61N 7/02 601/3 |

FOREIGN PATENT DOCUMENTS

| | | | |
|---|---|---|---|
| FR | 2903316 | A1 | 1/2008 |
| JP | 7047079 | | 2/1995 |
| JP | 2004147719 | A | 5/2004 |
| JP | 2004261253 | A | 9/2004 |
| WO | 180709 | A2 | 4/2001 |

OTHER PUBLICATIONS

French Search Report dated Dec. 6, 2011, corresponding to French Patent Application No. 1152657.

Non-English Office Action dated Apr. 3, 2015 for Chinese Application No. 201280016559.2 with an English translation.

* cited by examiner

METHOD AND APPARATUS FOR GENERATING FOCUSED ULTRASONIC WAVES WITH SURFACE MODULATION

This application is a 371 of PCT/FR2012/050544, filed on Mar. 15, 2012, which claims priority to French Patent Application No. 11 52657, filed Mar. 30, 2011.

The present invention relates to the technical field of apparatuses or devices including an ultrasonic probe formed by a plurality of ultrasonic transducer elements, suitable for emitting high intensity focused ultrasounds (HIFU).

The subject-mater of the present invention is particularly advantageously applicable in the field of therapeutic treatments using focused ultrasonic waves.

It is known that focused ultrasonic wave therapy makes it possible to create biological lesions in tissue resulting from a combination of the thermal effects and the acoustic cavitation activity. The shape of these tissue lesions results directly from the shape of the emission surface of the ultrasonic probe used. For example, an ultrasound probe with a spherical shape makes it possible to obtain a periodic focal zone, while a toroid-shaped probe leads to obtaining a ring- or crown-shaped focal zone.

At each point of the focal zone, it should be noted that the distances traveled by the ultrasonic waves from the emission surface are identical and that the pressure is directly related to the convergence of the ultrasonic waves at that point. In practice, the ultrasonic waves cross, between the emission surface and the focal zone, through various propagation mediums of different natures such as the water of a cooling circuit, the skin, fat, muscles, etc. However, these different mediums have different acoustic attenuation characteristics. Thus, for each of the traveled paths, an attenuation of the sonic waves appears that depends on the distance traveled in each of the crossed mediums.

Furthermore, after the emission in the propagation mediums, a focal effect is observed due to the concavity of the emission surface. The ultrasonic waves will concentrate on the focal zone (point or crown), leading to a gradual increase in the pressure along the path of the ultrasonic wave.

To try to do away with the drawbacks related to the acoustic heterogeneity of the tissues, it is known, for example from patent FR 2,642,640, to use a focusing device whereof the emission surface of the probe is divided into several transducer elements to which activation signals are applied, by means of control circuits, said signals being obtained by reversing the distribution over time and the shape of the echo signals received in return from an unfocused beam sent on the tissue to be treated. The transducer elements thus emit different acoustic powers depending on the attenuation and the focal effect of the acoustic waves.

In practice, the transducer elements have identical emission surfaces, such that each has the same electrical impedance. The control circuits of each of these transducer elements are also identical to facilitate the production of such a device.

However, this solution has a major drawback. In fact, the available electricity for each of the transducer elements is limited by the electronics of the control circuit. Thus, once one of the transducer elements operates at its maximum power to compensate the attenuation and focal difference of the ultrasonic waves, the other ultrasonic transducers must operate at a reduced electrical power and the electronics of the control circuit will not be able to provide the maximum power for which they were designed. In practice, the control circuit always, operates below its maximum capacity.

Also known from U.S. Pat. No. 4,888,746 is a therapeutic transducer made up of several transducer elements that can be actuated independently of one another by signals with variable amplitudes and phases so as to modulate the shape of the ultrasonic wave at the focal point in order in particular to reduce the cavitation effects.

Likewise, patent FR 2,903,616 describes a toroid-shaped therapeutic probe whereof the various transducer elements are activated sequentially to allow the ultrasonic waves to be focused in a crown.

The transducers described by these patents do not make it possible to homogenize the energy contributions made by the various ultrasonic transducer elements in a specific treatment area inasmuch as the focusing and attenuation effects undergone by the ultrasonic waves on their paths are not taken into account.

In the imaging field, U.S. Pat. No. 5,922,962 describes an ultrasonic transducer including a series of transducer elements having identical lengths but different widths. The widths of the transducer elements are determined so as to preserve the same ultrasonic beam profile, i.e., the same ultrasonic resolution, irrespective of the focal distance.

This document describes various beam formation techniques for dynamically focusing at different depths in the transmission and reception modes, as well as various apodization techniques for reducing the effects of side lobes. These beam formation techniques do not account for the acoustic attenuations of the ultrasonic waves on the path between the target zone and the transducer elements in order to obtain, in the target zone, a substantially identical energy contribution of the ultrasonic waves emitted by each of the transducer elements.

Similarly, documents U.S. Pat. No. 5,165,414, EP 0,689487 and EP 0,401,027 describe imaging transducers having the same drawbacks as the transducer described by U.S. Pat. No. 5,922,962. The transducers described by such documents do not aim to optimize the energy contributions of various transducer elements, inasmuch as an energy contribution is not sought in a target area for therapeutic reasons.

The present invention therefore aims to resolve the drawbacks of the state of the art by proposing a new technique for focusing ultrasonic waves making it possible to homogenize the energy contributions over a target zone in order to obtain the biological tissue lesions.

To achieve such an aim, the method for generating focused ultrasonic waves over a focal zone to produce biological lesions comprises the activation of a plurality of ultrasonic transducer elements distributed over an emission surface to respectively emit a plurality of focused ultrasonic waves in the focal zone, while crossing through the propagation mediums at different acoustic attenuations.

According to the invention:

- a target zone in which homogenization of the energy contributions of the ultrasonic waves emitted by the ultrasonic transducer elements is desired is chosen,
- the focal effect and the acoustic attenuations of the ultrasonic waves on their paths between the target zone and the ultrasonic transducer elements are determined,
- the focal effect and the acoustic attenuations of the ultrasonic waves are compensated, with ultrasonic transducer elements, at least some of which have non-identical emission surfaces so that in the target zone, the energy contribution of the ultrasonic waves emitted by the different ultrasonic transducer elements are substantially identical.

Furthermore, the method according to the invention may also have a combination of one or more of the following additional features:

- compensating the focal effects and the acoustic attenuations by assigning each of the ultrasonic transducer elements a surface weight factor depending on the acoustic attenuation and the focal effect undergone by the ultrasonic waves,
- determining the acoustic weight factors, taking into account the distance between the ultrasonic transducer elements and the separating zone of the propagation mediums,
- taking into account the distance between the ultrasonic transducer elements and the separating zone of the propagation mediums, calculating that distance as a function of the configuration of the propagation medium relative to said ultrasonic transducer elements,
- taking into account the distance between the ultrasonic transducer elements and the separating zone of the propagation mediums, measuring the echoes reflected following the sending of a calibration signal by the ultrasonic transducer elements,
- grouping together ultrasonic transducer elements with elementary sizes so as to form ultrasonic transducer elements with different emission surfaces configurable based on the encountered acoustic attenuations,
- for a plurality of ultrasonic transducer elements distributed on a concave emission surface with a radius of curvature Rc, calculating the area Sn of each ultrasonic transducer element n such that:

$$Sn=[S_{total}(1/(Fp(n)\cdot Z))]$$

with $S_{total}$: the sum of the surfaces of the ultrasonic transducer elements, $$Fp(n)=\text{Max } E(t)/\text{Max } E(n),$$

with Max E(t), the maximum value of the energy contribution of the transducer element t situated at the periphery of the emission surface and Max E(n), the maximum value of the energy contribution of the transducer element n in the target zone, Z: sum of the 1/Fp for all of the transducer elements.

Another aim of the invention is to propose a therapeutic apparatus for generating focused ultrasonic waves on a focal zone, including an ultrasonic probe formed by a plurality of ultrasonic transducer elements distributed on an emission surface to emit a plurality of ultrasonic waves focused in the focal zone, crossing through the propagation mediums with different acoustic attenuations, the ultrasonic transducer elements being excited by control signals coming from a control circuit, characterized in that at least some of the ultrasonic transducer elements have non-identical emission surfaces to emit focused ultrasonic waves which, in a target zone, have substantially identical energy contributions.

Furthermore, the apparatus according to the invention may additionally have a combination of one or more of the following additional features:

- at least some of the ultrasonic transducer elements are controlled by excitation signals with substantially identical values,
- the ultrasonic transducer elements are distributed according to a concave emission surface that may or may not be truncated,
- the ultrasonic transducer elements are distributed in rings or ring segments concentric to each other along the focal axis while having different emissions surfaces,
- the ultrasonic transducer elements are distributed on a planar surface.

Various other features emerge from the description provided below in reference to the appended drawings, which show, as non-limiting examples, embodiments of the subject-matter of the invention.

Figure 1:
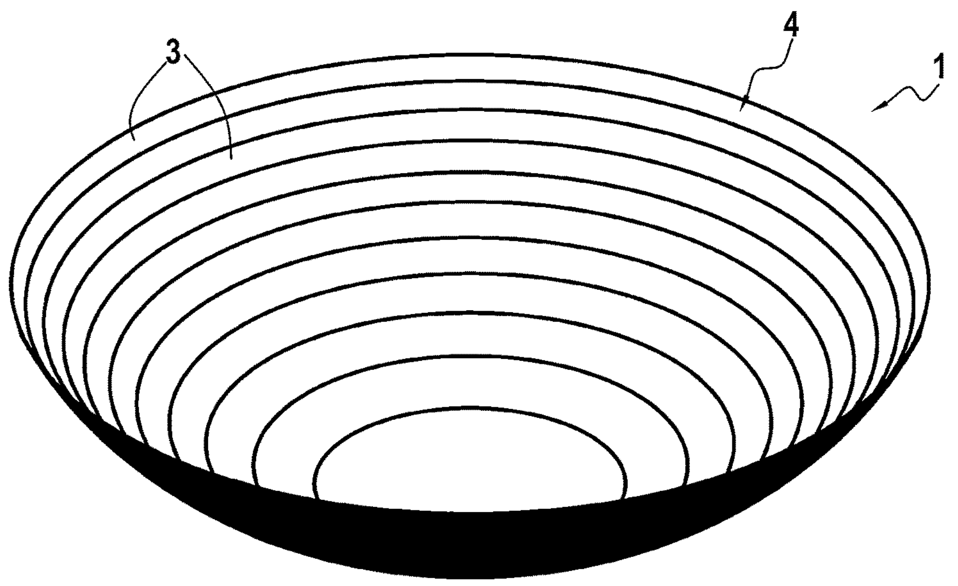
FIG. 1 is a perspective view of a first embodiment of a therapeutic probe according to the invention.
Figure 2:
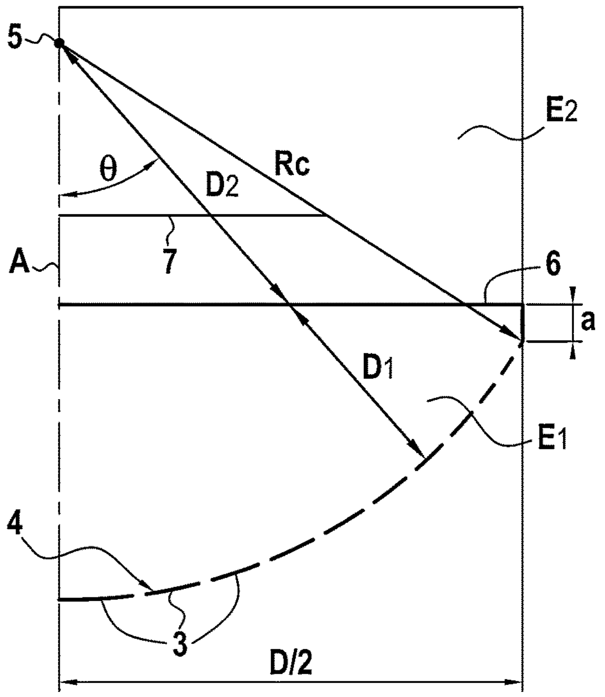
FIG. 2 is a diagrammatic view of an elevation half-cross-section of the therapeutic probe illustrated in FIG. 1 making it possible to describe the subject-matter of the invention.

FIGS. 1 and 2 illustrate a first example embodiment of the therapeutic ultrasonic probe 1 that is part of an apparatus for generating focused ultrasonic waves. The ultrasonic probe 1 includes a plurality of ultrasonic transducer elements 3 distributed along an emission surface 4. The ultrasonic transducer elements 3 are excited by control signals coming from a control circuit that is not shown but is known in itself and adapted so that the ultrasonic transducer elements 3 emit focused ultrasonic waves in a focal zone 5 to produce biological or tissue lesions. In the example illustrated in FIGS. 1 and 2, the ultrasonic transducer elements 3 are distributed along a concave emission surface 4 and are each in the shape of a ring or crown. The ultrasonic transducer elements 3 are therefore mounted concentrically relative to one another and relative to the focal axis X.

According to the invention, at least some of the ultrasonic transducer elements 3 have non-identical emission surfaces to emit focused ultrasonic waves which, in a target zone 7, have substantially identical energy contributions. In other words, the ultrasonic transducer elements 3 have emission surfaces of different values to compensate the focal and acoustic attenuation differences undergone by the ultrasonic waves during their path between the transmission surface 4 and the target zone 7. This target zone 7 may thus be chosen, as will be shown later in the description, in any location situated starting from the emission surface 4 and as far as the focal zone 5, the latter being the target zone 7 in one advantageous alternative embodiment.

In fact, it must be considered that the ultrasonic waves cross, from the emission surface 4 to the target zone 7, several propagation mediums $E_1$, $E_2$ . . . $E_i$ . . . $E_k$, each having acoustic attenuations $A_1$, $A_2$ . . . $A_i$, . . . $A_k$, respectively. As an example, FIG. 2 illustrates the interposition between the focal zone 5 and the probe 1 of a first propagation medium $E_1$ in contact with the emission surface 4, having acoustic attenuation $A_1=0$, and a second medium $E_2$ situated at a distance a from the plane tangent to the probe. The first propagation medium $E_1$ and the second propagation medium $E_2$ have a separating zone or an interface 6. The second medium $E_2$, which has an acoustic attenuation $A_2$ (with $A_2 \neq A_1$), extends at least as far as the focal zone 5. The target zone 7 is a plane situated, in the example illustrated in FIG. 2, in the second medium $E_2$, between the focal zone 5 and the interface 6.

During the travel of the ultrasonic wave between the emission surface 4 and the focal zone 5, two phenomena, from the pressure perspective, remain in play, the geometric focusing effect and the acoustic attenuation. The focusing effect is due to the concavity of the emission surface 4, leading to a major increase in the pressure along the path of the ultrasonic wave, while the acoustic attenuation, which represents the transfer of energy from the ultrasonic wave to its propagation medium, primarily depends on the absorptive properties of the propagation medium, amounting to a pressure decrease during the traveled path.

The pressure of an ultrasonic wave between the target zone 7 and the probe 1 depends on the distance traveled by the waves in each of the mediums $E_1$, $E_2$ and has the following expression (1):

$$P(r) = P_0 \cdot \prod_{i=1}^{i=k} (e^{-A_i \cdot D_i}) \cdot \frac{Rc}{Rc - r}$$

Ei: propagation medium with i=1 at k, $D_i$: distance traveled in the propagation medium Ei (m), P(r): pressure at the distance r from the emission surface ($P_a$), Rc: radius of curvature of the transducer element (m), $P_0$: pressure during the emission (Pa), Ai: acoustic absorption of the propagation medium Ei ($Np \cdot m^{-1}$)

In order to calculate the pressure in the target zone 7, only the attenuation and the focusing effect were taken into account. It is of course possible to refine the model by considering any other effect in play during the ultrasonic emission, in particular the diffraction with a Rayleigh model, for example.

In the case where the ultrasonic wave passes through two mediums $E_1$, $E_2$ between the emission surface 4 and the target zone 7, the expression is as follows:

$$P(r)=P_0 e^{-A1*D1} \cdot e^{-A2*D2} \cdot Rc/(Rc-r)$$

Figure 3A:
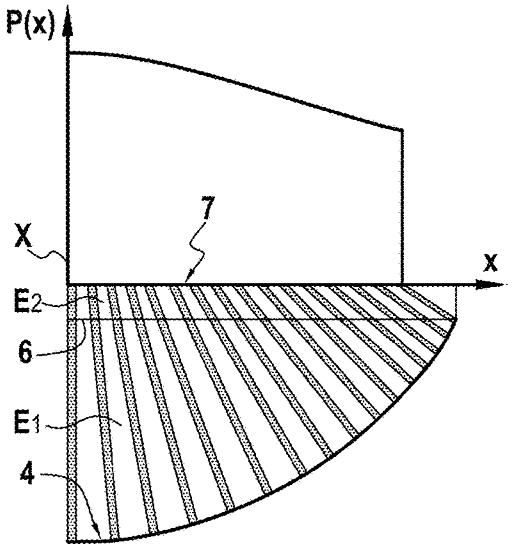
FIGS. 3A to 3D are diagrammatic elevation half-cross-section of views of the therapeutic probe illustrated in FIG. 1 and respectively showing the focal effect, the acoustic absorption effect, the combination of the focal and absorption effects, the rebalancing of the energy contribution in a target zone by applying the invention.
Figure 3B:
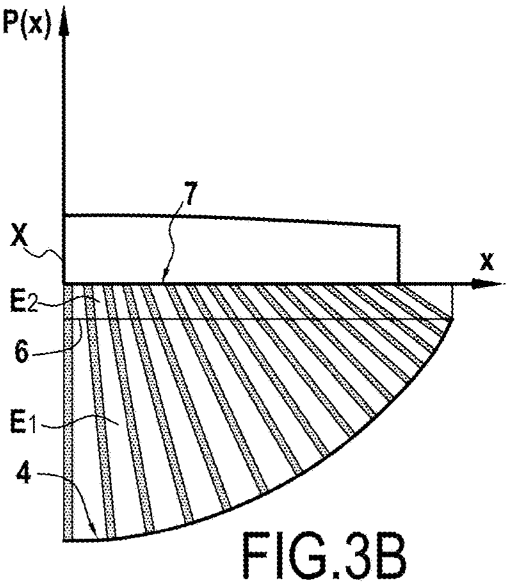

At the target zone 7, it must be noted, as illustrated in FIG. 3A, that there is an inequality of the energy contributions within that zone along the axis x, since the focal effect is stronger at the center of that zone and weaker on the periphery. Furthermore, this phenomenon is increased by the acoustic attenuation, as illustrated in FIG. 3B. In the case where the first medium $E_1$ (water, for example) has a zero acoustic attenuation, the ultrasonic probes not being attenuated in the medium $E_1$, then those ultrasonic waves all have the same intensity when they arrive at the interface 6 (i.e., for example the skin). Beyond the interface 6, the distances traveled are unequal, such that the ultrasonic waves emitted by a transducer element situated at the periphery of the emission surface have a greater distance to travel than those emitted from the renter of the emission surface and are therefore attenuated if one moves away from the focal axis x. Ultimately, the combination of these two phenomena gives rise to the pressure curve $P_1$ illustrated in FIG. 3C. This pressure curve shows a pressure inequality of the target zone 7 (i.e., the skin in considered example), this pressure inequality being able to lead to the creation of burns near the focal axis x.

Given that the focal effect and the attenuation undergone by the ultrasonic waves are different based on their emission location on the probe 1, an inequality results, at the target zone 7, in terms of energy contribution provided by the different ultrasonic waves.

According to the invention, this inequality in terms of energy contribution in the target zone 7 is compensated by assigning the ultrasonic transducer elements 3 surfaces with different sizes or values. It should be noted that all of the ultrasonic transducer elements 3 are controlled by excitation signals with substantially identical values. In other words, the same power instruction is applied to all of the ultrasonic transducer elements 3, it therefore appears possible for the probe to use all of the available power.

The method according to the invention thus alms to determine a surface weighting factor $f_s$ for each of the ultrasonic transducer elements 3, such that:

$$F_s(n)=1/[F_p(n) \cdot Z]$$

with $0<F_s<1$ n: the number of the transducer element 3 and varying from 1 to t in the direction going from the focal axis X toward the periphery of the emission surface 4, $F_p$: the power factor, Z: the sum of the transducer elements of the $1/F_p$.

The power factor $F_p(n)$ is expressed based on the focal effect and the acoustic attenuations on each ultrasonic transducer element 3 between the transducer element and the target zone 7, during the division of the emission surface into equal surfaces (before modulation).

The power factor $F_p(n)$ can be expressed as follows:

$$F_p(n)=\text{Max } E(t)/\text{Max } E(n)$$

Max E(t): maximum value of the energy contribution of the transducer element t situated at the periphery of the emission surface 4, Max E(n): maximum value of the energy contribution of the transducer element n in the target zone 7.

The area with surface S(n) of each ultrasonic transducer element 3 of rank n is such that:

$$S(n)=S_{total} F_s(n)$$

with $S_{total}$, the total surface area of the probe.

It emerges from the above expressions that the transducer elements 3 close to the center of the probe (of the focal axis X) have a larger surface relative to the transducer elements 3 close to the periphery of the probe. Thus, the surface of the transducer elements 3 increases for the transducer elements 3 close to the center, and conversely, decreases for the transducer elements close to the periphery of the probe.

The application of these different surface weight factors $F_s$ for the ultrasonic transducer elements 3 causes a modification in the pressure field and thus makes it possible to rebalance the energy contribution of each of the ultrasonic transducer elements 3 in the target zone 7. As emerges from FIG. 3D, the energy contribution of the ultrasonic waves emitted by the different ultrasonic transducer elements 3 is substantially identical in the target zone 7 (curve $P_2$) despite the focal effect and the acoustic attenuations undergone by the ultrasonic waves on their path.

In the example illustrated in FIG. 2, the ultrasonic waves pass through two acoustic attenuation mediums whereof the interface 6 between the mediums is planar, parallel to the plane tangent to the probe. Of course, the number of acoustic attenuation mediums crossed by the ultrasonic waves may be higher. Likewise, the shape of the interface 6 between the acoustic attenuation mediums may be different from a plane parallel to the plane tangent to the probe.

Figure 4:
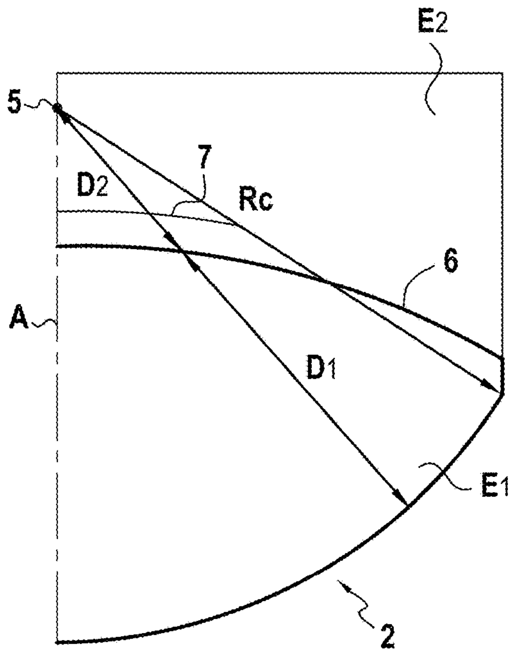
FIGS. 4 and 5 are elevation half-cross-sectional diagrams making it possible to explain one alternative according to the invention.

FIG. 4 illustrates an example in which the interface 6 between the two acoustic attenuation mediums $E_1$, $E_2$ has a convex shape. In fact, in FIG. 4, the volume of water (acoustic attenuation medium $E_1$) is higher, such that the focal and attenuation contrast is more significant. The contrast of the energy contributions is accentuated for a convex interface 6 relative to a planar interface.

Figure 5:
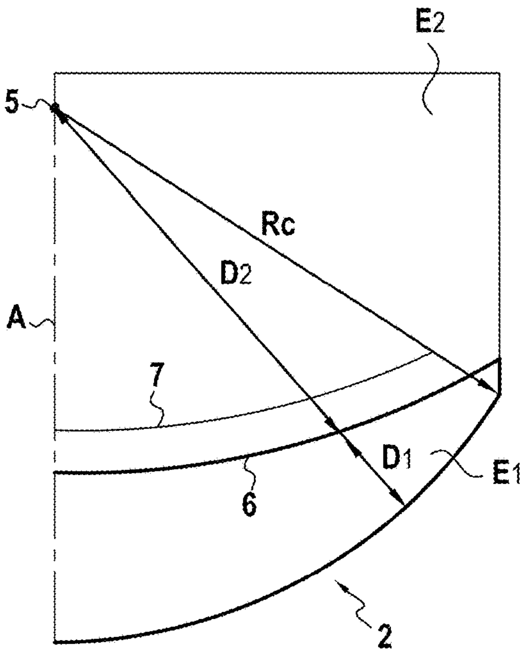

On the contrary, a concave interface 6 as illustrated in FIG. 5 leads to rebalancing of the energy contributions relative to the example illustrated in FIG. 2. Of course, in the specific case where the interface 6 between the acoustic mediums and the target zone 7 has the same center of curvature as the emission face of the probe 1, the energy contributions of the ultrasonic transducer elements are identical in the target zone 7.

In general, it must be considered that the method according to the invention aims to choose a target zone 7 in which a homogenization of the energy contributions of the ultrasonic waves emitted by the ultrasonic transducer elements 3 is desired. According to a first preferred alternative embodiment, this target zone corresponds to the focal zone. According to a second preferred alternative embodiment, this target zone corresponds to a plane included in a propagation medium and in particular in the second propagation medium, corresponding to the tissue situated between the cooling water and the tissue to be treated.

The method according to the invention aims to determine the focal effect as well as the acoustic attenuations of the ultrasonic waves on their path between said target zone 7 and the ultrasonic transducer elements 3. As explained above, this determination phase consists of taking into account the focal effect and the acoustic attenuations of the various propagation mediums crossed and the distance between the ultrasonic transducer elements 3 and the interface(s) between the mediums. This distance may be calculated as a function of the configuration of the propagation medium(s) relative to the ultrasonic transducer elements 3. It should be noted that the distance between the ultrasonic transducer elements 3 and the interface of the mediums may be determined more precisely by measuring echoes reflected in mode A, which consists of measuring echoes reflected following the sending of a calibration signal by the ultrasonic transducer elements 3.

Figure 3C:
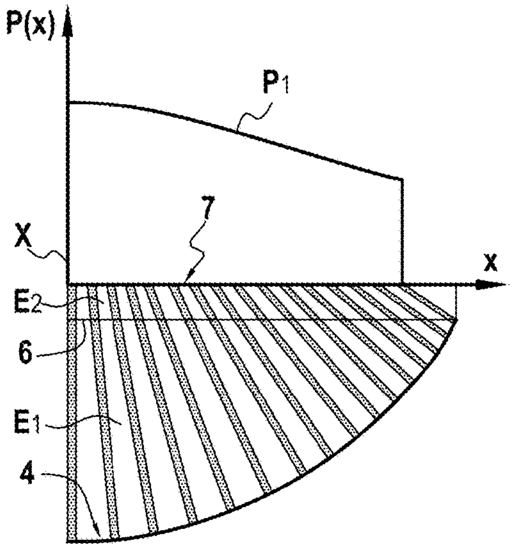
Figure 3D:
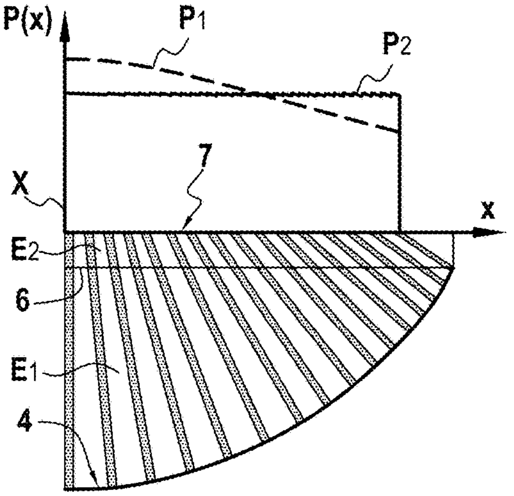

On first approximation, from equation (1), the pressure may be calculated in the target zone 7 for a multitude of ultrasonic waves coming from the emission surface making it possible to obtain the pressure curve $P_1$ illustrated in FIG. 3C.

The emission surface 4 is divided up from the focal axis x to its peripheral part. In the case of an emission surface 4 of revolution, the emission surface 4 is divided into concentric rings each contributing to part of the pressure curve $P_1$. For each ring, the maximum pressure value is determined and a surface weight factor $F_s$ is applied such that said maximum pressure value becomes identical over all of the elements (curve $P_2$).

The method according to the invention therefore makes it possible to modulate the emission surface of the ultrasonic transducer elements 3 into areas of different sizes but adapted so that the energy contribution of the ultrasonic waves is substantially identical in the target zone 7. Thus, the different transducer elements 3 are configured with emission surfaces having different values adapted to one or more given applications. It should be noted that the higher the number of ultrasonic transducer elements 3, the more precise and effective the modulation.

Figure 6:
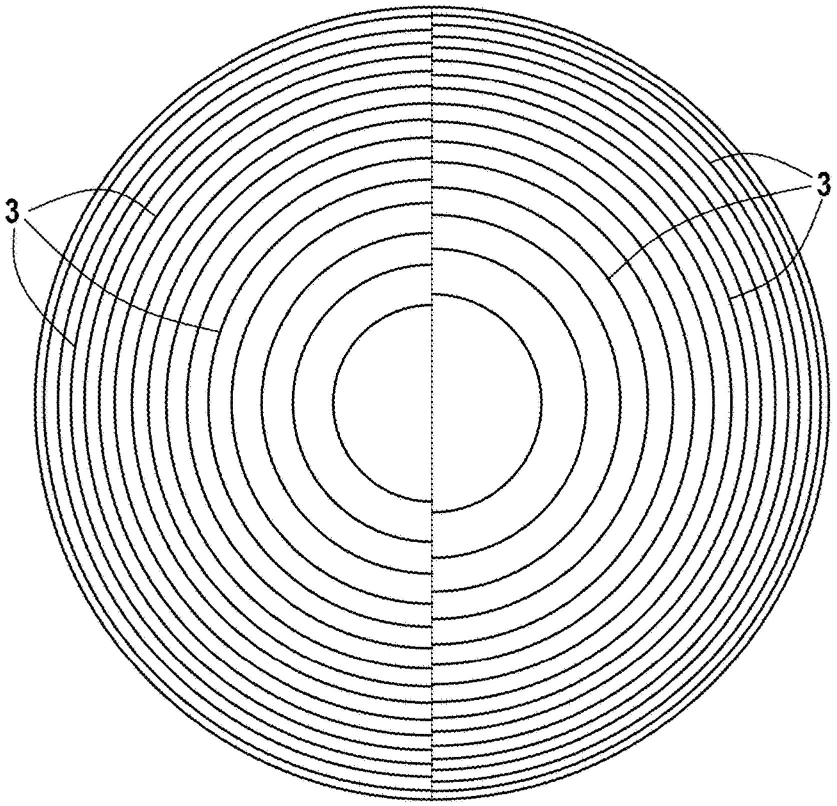
FIG. 6 is a top view, the left part showing the distribution of the ultrasonic transducer elements of the prior art and the right side showing the distribution of the ultrasonic transducer elements according to the invention.

FIG. 6 illustrates the division of a focusing probe having transducer elements 3 in the shape of rings. The left part of FIG. 6 shows ultrasonic transducer elements of equal surfaces whereas the right part of FIG. 6 has ultrasonic transducer elements 3 with different surfaces modulated using the method according to the invention.

Figure 7:
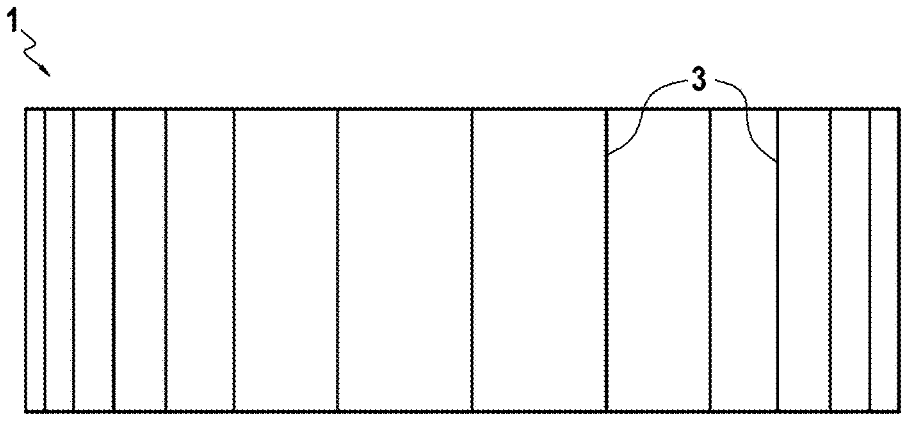
FIG. 7 shows an example embodiment of a therapeutic program according to the invention of the planar type.

Of course, the method according to the invention may be used for therapeutic probes of various shapes. In the example illustrated in FIG. 1, the ultrasonic transducer elements 3 are distributed over a complete concave emission surface of revolution. For determined applications, this concave surface may be truncated on either side of a central plane of symmetry such that the ultrasonic transducer elements 3 are distributed in the ring segments concentric to each other. According to one preferred alternative embodiment, this concave surface is in the shape of a toroid, i.e., this concave surface is created by rotating a concave curve segment with a finite length around an axis of symmetry located at a non-zero distance from the center of curvature of the concave curve segment. Of course, this torpid-shaped emission surface may be truncated on either side of a central plane of symmetry. According to another alternative embodiment, the concave emission surface results from a cylindrical geometry created by translating two concave curve segments with a finite length, which are symmetrical relative to a plane of symmetry, the translation being done along a limited length and in a direction perpendicular to the plane containing said concave curve segments. FIG. 7 illustrates, as an example, a planar probe 1 whereof the different ultrasonic transducer elements 3 have emission surfaces of different sizes.

Of course, in the case of a planar therapeutic probe 1, each ultrasonic transducer element is supplied by signals having phase shifts making it possible to obtain a focal effect in the target zone.

Figure 7A:
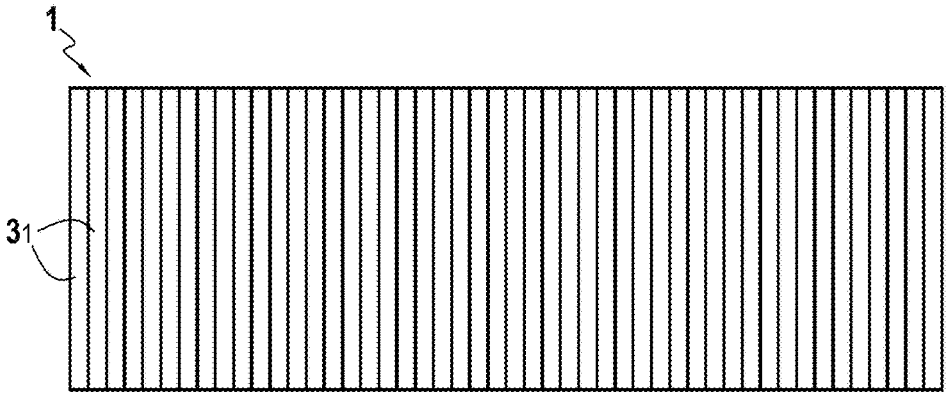
FIGS. 7A and 7B show another alternative embodiment of the probe described in FIG. 7, with FIG. 1A illustrating the probe with elementary ultrasonic transducer elements with the same surface which, in FIG. 7B, are electronically assembled to have a surface modulation identical to that illustrated in FIG. 7.
Figure 7B:
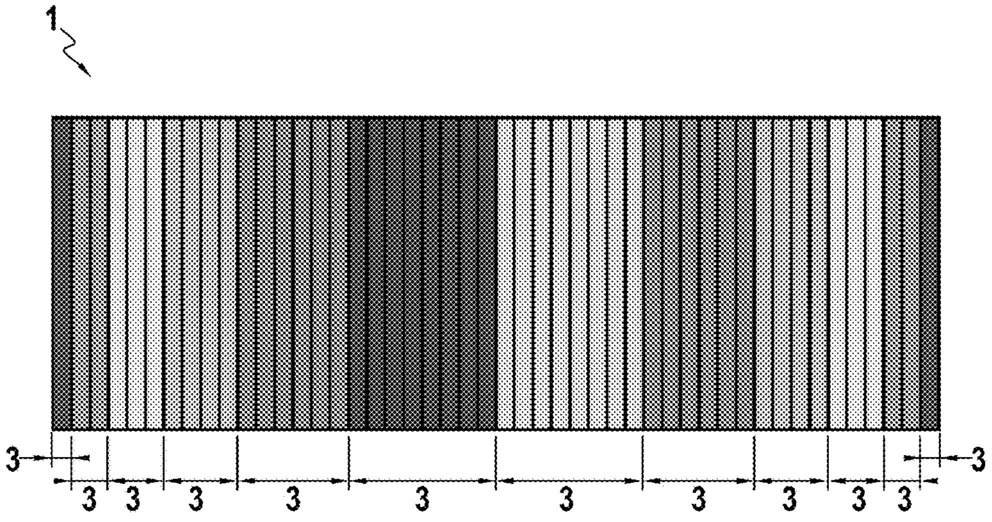

Another subject-matter of the invention is to be able to propose a technique making it possible to produce a probe configurable on demand based on the configuration of the propagation mediums of the ultrasonic probes. As emerges more precisely from FIGS. 7A, 7B, this technique provides for choosing an elementary size for all of the ultrasonic transducer elements $\mathbf{3}_1$. Thus, in the example illustrated in FIG. 7A illustrating a planar emission surface, all of the elementary ultrasonic transducer elements $\mathbf{3}_1$ have the same emission surface. These elementary ultrasonic transducer elements 3 are then grouped together so as to produce ultrasonic transducer elements 3 that have different sizes (FIG. 7B). Thus, this technique makes it possible to create, on demand, ultrasonic transducer elements 3 having different emission surfaces. It should be noted that in the case of a concave emission surface, the ultrasonic transducer elements $\mathbf{3}_1$ may have different elementary sizes, with an identical width fir all of the ultrasonic transducer elements.

The invention is not limited to the examples described and shown, as various changes may be made thereto without going beyond the scope of the invention.

The invention claimed is:

1. A method for generating focused ultrasonic waves over a focal zone to produce biological lesions comprising an activation of a plurality of ultrasonic transducer elements distributed over an emission surface to respectively emit a plurality of focused ultrasonic waves in the focal zone, while crossing through propagation media at different acoustic attenuations, the method comprising:

choosing a target zone in which homogenization of contributions of the ultrasonic waves emitted by the plurality of ultrasonic transducer elements during said activation is desired, calculating a pressure in the target zone by determining a focal effect and acoustic attenuations of the ultrasonic waves on paths of the ultrasonic waves between the target zone and the plurality of ultrasonic transducer elements, during at least one activation period, compensating the focal effect and the acoustic attenuations of the ultrasonic waves with the plurality of ultrasonic transducer elements, wherein at least some of the plurality of ultrasonic transducer elements have non-identical emission surfaces, and during said activation period, controlling each of the plurality of ultrasonic transducer elements by excitation signals with substantially identical values, wherein the energy contribution, in the target zone, of the ultrasonic waves emitted by the different ultrasonic transducer elements, during said activation, are substantially identical, to produce biological or tissue lesions;

wherein the plurality of ultrasonic transducer elements are distributed on a concave emission surface.

2. The method according to claim 1, comprising compensating the focal effects and the acoustic attenuations by assigning each of the plurality of ultrasonic transducer elements a surface weight factor depending on the acoustic attenuation and the focal effect undergone by the ultrasonic waves.

3. The method according to claim 2, comprising determining the surface weight factor by taking into account a distance between the plurality of ultrasonic transducer elements and a separating zone of the propagation media.

4. The method according to claim 3, comprising taking into account the distance between the plurality of ultrasonic transducer elements and the separating zone of the propagation media by calculating that distance as a function of a configuration of the propagation media relative to said plurality of ultrasonic transducer elements.

5. The method according to claim 3, comprising taking into account the distance between the plurality of ultrasonic transducer elements and the separating zone of the propagation media by measuring echoes reflected following sending of a calibration signal by the plurality of ultrasonic transducer elements.

6. The method according to claim 1, comprising grouping together ultrasonic transducer elements with elementary sizes, thereby forming ultrasonic transducer elements with different emission surfaces configurable based on the encountered acoustic attenuations.

7. The method according to claim 1, comprising, for the plurality of ultrasonic transducer elements distributed on a concave emission surface with a radius of curvature Rc, calculating a surface area Sn of each ultrasonic transducer element n such that:

$$Sn=[S\text{total}(1/(Fp(n)\cdot Z))]$$

where Fp=power factor, with Stotal: the sum of the surface areas of the plurality of ultrasonic transducer elements, $$Fp(n)=\text{Max } E(t)/\text{Max } E(n),$$

with Max E(t), the maximum value of the energy contribution of the transducer element t situated at a periphery of the emission surface and Max E(n), the maximum value of the energy contribution of the transducer element n in the target zone, Z: sum of the 1/Fp(n) for all of the transducer elements.

8. A therapeutic apparatus for generating focused ultrasonic waves on a focal zone, the apparatus comprising:

an ultrasonic probe formed by a plurality of ultrasonic transducer elements distributed on an emission surface that is configured to emit a plurality of ultrasonic waves focused in the focal zone, crossing through the propagation media with different acoustic attenuations, wherein the plurality of ultrasonic transducer elements are configured to be excited by control signals coming from a control circuit, wherein at least some of the plurality of ultrasonic transducer elements are configured to have non-identical emission surfaces, wherein each of the plurality of ultrasonic transducer elements are controlled, during said activation, by excitation signals with substantially identical values, the plurality of ultrasonic transducer elements being configured and controlled to emit focused ultrasonic waves, and wherein the plurality of ultrasonic transducer elements are further configured and controlled to have substantially identical energy contributions in a target zone, and produce biological or tissue lesions, and wherein the plurality of ultrasonic transducer elements are distributed on a concave emission surface resulting from a cylindrical geometry created by translating two concave curve segments with a finite length, which are symmetrical relative to a plane of symmetry, the translation being done along a limited length and in a direction perpendicular to a plane containing said concave curve segments.

9. The apparatus according to claim 8, wherein the ultrasonic transducer elements are distributed according to a concave emission surface that may or may not be truncated.

10. The apparatus according to claim 8, wherein the ultrasonic transducer elements are distributed in rings or ring segments concentric to each other along a focal axis while having emissions surfaces with different values.

11. The apparatus according to claim 8, wherein the ultrasonic transducer elements are distributed on a planar surface.

12. The apparatus according to claim 8, wherein the ultrasonic transducer elements are distributed according to a concave emission surface in the shape of a toroid.

13. The apparatus according to claim 8, wherein the ultrasonic transducer elements are distributed according to a concave emission surface in the shape of a truncated toroid.

* * * * *

UNITED STATES PATENT AND TRADEMARK OFFICE

CERTIFICATE OF CORRECTION

PATENT NO. : 9,936,969 B2
APPLICATION NO. : 14/007918
DATED : April 10, 2018
INVENTOR(S) : Jeremy Vincenot et al.

It is certified that error appears in the above-identified patent and that said Letters Patent is hereby corrected as shown below:

On the Title Page

Delete title page and replace with attached title page.

In the Claims

Claims 9-13 should be deleted.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

(12) United States Patent
Vincenot et al.
(10) Patent No.: US 9,936,969 B2
(45) Date of Patent: Apr. 10, 2018

(54) METHOD AND APPARATUS FOR GENERATING FOCUSED ULTRASONIC WAVES WITH SURFACE MODULATION

(75) Inventors: Jeremy Vincenot, Les Haies (FR); David Melodelima, Ruy (FR); Emmanuel Blanc, Saint-Didier au Mont d'Or (FR); Jean-Yves Chapelon, Villeurbanne (FR)

(73) Assignees: EDAP TMS FRANCE, Vaulx-en-Velin (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 554 days.

(21) Appl. No.: 14/007,918

(22) PCT Filed: Mar. 15, 2012

(86) PCT No.: PCT/FR2012/050544

§ 371 (c)(1),
(2), (4) Date: Dec. 3, 2013

(87) PCT Pub. No.: WO2012/131212

PCT Pub. Date: Oct. 4, 2012

(65) Prior Publication Data

US 2014/0180320 A1 Jun. 26, 2014

(30) Foreign Application Priority Data

Mar. 30, 2011 (FR) .............................. 11 52657

(51) Int. Cl.
*A61B 17/32* (2006.01)
*G10K 11/32* (2006.01)

(52) U.S. Cl.
CPC ...... *A61B 17/320068* (2013.01); *G10K 11/32* (2013.01)

(58) Field of Classification Search
CPC .......... A61B 8/4477-8/4494; A61N 2007/0065
See application file for complete search history.

(56) References Cited

U.S. PATENT DOCUMENTS 4,281,550 A * 8/1981 Erikson ............... G01N 29/262 310/334
4,470,308 A * 9/1984 Hayakawa ........... B06B 1/0633 367/150

(Continued)

FOREIGN PATENT DOCUMENTS

EP 0401027 A2 12/1990
EP 0689187 B1 1/2002

(Continued)

OTHER PUBLICATIONS

International Search Report dated Jul. 23, 2012, corresponding to PCT/FR2012/050544.

(Continued)

*Primary Examiner* — Serkan Akar
(74) *Attorney, Agent, or Firm* — Ladas & Parry LLP

(57) ABSTRACT

The invention relates to a method for generating ultrasonic waves focused on a focal zone (5) in order to carry out biological lesions, comprising the activation of a plurality of ultrasonic transducer elements (3).
According to the invention:
a target zone, in which homogenization of the supply of energy of the ultrasonic waves emitted by the ultrasonic transducer elements is desired, is chosen,
the focusing effect and the acoustic attenuations of the ultrasonic waves on their path between the target zone and the ultrasonic transducer elements (3) are determined,
the focusing effect and the acoustic attenuations of the ultrasonic waves are compensated, with ultrasonic transducer elements (3) at least some of which have (Continued)

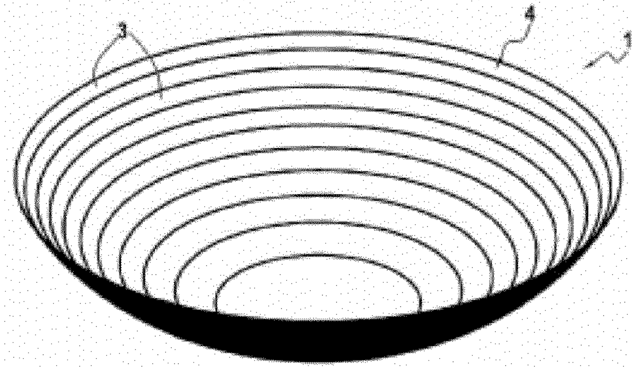

US 9,936,969 B2

Page 2 non-identical emission surfaces such that in the target zone, the supply of energy of the ultrasonic waves emitted by the different ultrasonic transducer elements (3) is more or less identical.

8 Claims, 4 Drawing Sheets

(56) References Cited

U.S. PATENT DOCUMENTS

| | | | | |
|---|---|---|---|---|
| 4,888,746 A | | 12/1989 | Wurster et al. | |
| 5,165,414 A | | 11/1992 | Larson | |
| 5,922,962 A | | 7/1999 | Ishrak et al. | |
| 6,328,695 B1 | * | 12/2001 | Vammen | A61B 8/0875 600/442 |
| 6,543,272 B1 | * | 4/2003 | Vitek | A61N 7/02 601/2 |
| 7,678,054 B2 | | 3/2010 | Okazaki et al. | |
| 2007/0106157 A1 | * | 5/2007 | Kaczkowski | A61B 5/015 600/438 |
| 2009/0281463 A1 | * | 11/2009 | Chapelon | A61N 7/02 601/2 |
| 2012/0191020 A1 | * | 7/2012 | Vitek | A61N 7/02 601/3 |

FOREIGN PATENT DOCUMENTS

| | | |
|---|---|---|
| FR | 2903316 A1 | 1/2008 |
| JP | 7047079 | 2/1995 |
| JP | 2004147719 A | 5/2004 |
| JP | 2004261253 A | 9/2004 |
| WO | 180709 A2 | 4/2001 |

OTHER PUBLICATIONS

French Search Report dated Dec. 6, 2011, corresponding to French Patent Application No. 1152657.

Non-English Office Action dated Apr. 3, 2015 for Chinese Application No. 201280016559.2 with an English translation.

* cited by examiner